United States Patent
Chilakala et al.

(10) Patent No.: US 11,642,358 B1
(45) Date of Patent: May 9, 2023

(54) STABLE PHARMACEUTICAL FORMULATION

(71) Applicant: EXTROVIS AG, Baar (CH)

(72) Inventors: Krishna Mohan Chilakala, Hyderabad (IN); Hanumantha Rao Kamma, Baar (CH); Janos Vaczi, Kuessnacht am Rigi (CH)

(73) Assignee: EXTROVIS AG, Baar (CH)

( * ) Notice: Subject to any disclaimer, the term of this patent is extended or adjusted under 35 U.S.C. 154(b) by 0 days.

(21) Appl. No.: 17/712,524

(22) Filed: Apr. 4, 2022

(30) Foreign Application Priority Data

Feb. 14, 2022 (IN) .............................. 202221007615

(51) Int. Cl.
| | | |
|---|---|---|
| *A01N 43/00* | (2006.01) | |
| *A01N 43/46* | (2006.01) | |
| *A61K 31/55* | (2006.01) | |
| *A61K 31/675* | (2006.01) | |
| *A61K 47/20* | (2006.01) | |
| *A61K 47/10* | (2017.01) | |

(52) U.S. Cl.
CPC ............ *A61K 31/675* (2013.01); *A61K 47/10* (2013.01); *A61K 47/20* (2013.01)

(58) Field of Classification Search
CPC .................................................. A61K 31/675
See application file for complete search history.

(56) References Cited

U.S. PATENT DOCUMENTS

| | | |
|---|---|---|
| 9,662,342 B2 | 5/2017 | Palepu et al. |
| 10,849,916 B2 | 12/2020 | Shaik et al. |
| 2017/0143744 A1 | 5/2017 | Shaik et al. |
| 2018/0055861 A1 | 3/2018 | Chandrashekhar et al. |

FOREIGN PATENT DOCUMENTS

| | | | |
|---|---|---|---|
| WO | WO-2016132270 A1 * | 8/2016 | ........... A61K 31/675 |
| WO | 2020/178725 A1 | 9/2020 | |

OTHER PUBLICATIONS

AuroMedics Pharma LLC, "Cyclophosphamide—cyclophosphamide injection," Drug Label Information updated Aug. 2021. Accessible at web page <https://dailymed.nlm.nih.gov/dailymed/drugInfo.cfm?setid=3c1eb470-0bba-457d-94e3-b9508f0d398a>.

Ingenus Pharmaceuticals, LLC, "Cyclophosphamide—cyclophosphamide injection, solution," Drug Label Information updated Sep. 2021. Accessible at web page <https://dailymed.nlm.nih.gov/dailymed/drugInfo.cfm?setid=783d7523-8505-4b3e-837c-cefbcec61da6>.

Baxter Healthcare Corporation, "Cyclophosphamide injection, for intravenous use Cyclophosphamide tablets, for oral use," Drug Label Information updated May 2013. Accessible at web page <https://www.accessdata.fda.gov/drugsatfda_docs/label/2013/012141s090,012142s112lbl.pdf>.

\* cited by examiner

*Primary Examiner* — Layla Soroush
(74) *Attorney, Agent, or Firm* — Medler Ferro Woodhouse & Mills PLLC

(57) ABSTRACT

The present invention relates to a stable formulation of cyclophosphamide comprising a therapeutically effective amount of cyclophosphamide, ethanol as solvent, polyethylene glycol as the solvent, and optionally, monothioglycerol as the anti-oxidant, wherein the composition is stable over its shelf life.

10 Claims, No Drawings

STABLE PHARMACEUTICAL FORMULATION

The present invention relates to a stable formulation of cyclophosphamide comprising a therapeutically effective amount of cyclophosphamide, ethanol as solvent, polyethylene glycol as the solvent, and optionally, monothioglycerol as the anti-oxidant, wherein the composition is stable over its shelf life.

BACKGROUND

Cyclophosphamide, also known as cyclophosphane is a medicine used in the treatment of cancer. It is used as chemotherapy to suppress the immune system. It is used to treat conditions such as lymphoma, multiple myeloma, leukaemia, ovarian cancer, breast cancer, small cell lung cancer, neuroblastoma, sarcoma and for minimal change nephrotic syndrome in pediatric patients.

Cyclophosphamide is the generic name for the brand Cytoxan or Neosar, and has the following structure—

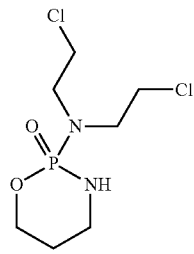 [SMILES: O=P1(N(CCCl)CCCl)NCCCO1]

The IUPAC name for cyclophosphamide is N, N-bis (2-chloroethyl)-1, 3, 2-oxazaphosphinan-2-amine 2-oxide.

The product is commercially available as a lyophilized product, that needs to be reconstituted with a suitable solvent, followed by withdrawal of the required dose from the vial and mixing with a large volume of parenteral solution so that it can be administered to the patient as an infusion. There are several precautions to be taken before infusion of the drug. Those handling the preparation need to wear protective gloves. One should take care that the preparation does not splash in the eyes. The choice of solvent for reconstituting cyclophosphamide depends on the route of administration to be used. If the solution is to be used for intravenous (IV) infusion, it is reconstituted by adding sterile water for injection or 0.9% sterile sodium chloride solution. Reconstituted cyclophosphamide should be further diluted in 5% dextrose or 0.9% sodium chloride solution prior to infusion. In the case of direct injection, cyclophosphamide is reconstituted by adding 0.9% sterile sodium chloride solution. Only cyclophosphamide reconstituted in 0.9% sterile sodium chloride is suitable for bolus injection. To reduce the chances of any adverse reactions that appear to be dependent on administration rate, (e.g. facial swelling, headache, nasal congestion, scalp burning), cyclophosphamide should be injected very slowly in the range of 30 minutes to 2 hours. This range would also be dependent on the volume and type of carrier fluid to be infused.

It is well known that there could be exposure to carcinogenic cytotoxic agents during the preparation of reconstituted solutions of such agents. There is always a chance of contaminating the nursing staff and the compounding area. Further, the reconstitution process could lead to errors, thereby leading to under or overdosing (dosing errors). It must also be noted that a lyophilized product that requires reconstitution, followed by withdrawal of desired dose and dilution with a large volume parenteral, leads to creation of significant amount of oncologic waste, such as syringes, vials, gloves, needles, masks and equipment. Further, biomedical waste of genotoxic category is extremely hazardous to the environment and human health due to its carcinogenic potential. The exposure to these drugs through skin contact, absorption, inhalation, ingestion and needle injuries may cause hair loss, liver damage vomiting, fetal loss in pregnant woman, birth malformation in the children of pregnant women, abnormal formation of cells, alteration to normal blood cell count, and countless other side effects. Hence, there are serious safety issues associated with the handling and disposal of cytotoxic waste. It is also important to note that the cost of disposal of the carcinogenic waste is significant, and any effort that can reduce the waste would mean cost saving.

In light of the above, there is a need for ready-to-use or ready-to-dilute formulations of cyclophosphamide. This would help avoid the step of reconstitution and handling, and would eventually also reduce the oncogenic waste created. In order to make such formulations, a suitable solvent system is essential, along with a packaging system that is robust and maintains the stability of the product. Cyclophosphamide must not degrade in the solvent and must remain stable throughout its shelf life.

US20180055861 (Leiutis, now granted as U.S. Ser. No. 10/993,952), relates to a stable, ready to dilute, liquid parenteral formulation of cyclophosphamide and process for preparation thereof. The publication discloses a stable non-aqueous liquid parenteral formulation of cyclophosphamide comprising cyclophosphamide, one or more solvents selected from alcohols such as ethanol, propylene glycol, polyethylene glycol, dimethyl acetamide, glycerol or mixtures thereof, and optionally other pharmaceutically acceptable adjuvants. The claims of the granted U.S. Ser. No. 10/993,952 cover a stable liquid parenteral formulation of cyclophosphamide comprising i) cyclophosphamide in a concentration of about 12% to about 23% based on total formulation weight; ii) an ethanol content of about 70% to about 75% based on total formulation weight; iii) both polyethylene glycol and propylene glycol, wherein the polyethylene glycol to propylene glycol mass ratio is between approximately 1.0:1.0 to approximately 2.0:1.0; and iv) about 3.4% to about 8.8% based on total formulation weight of polyethylene glycol v) about 3.4% to about 4.4% based on total formulation weight of propylene glycol vi) wherein, after storage for 7 days at 40.degree. C./75% RH, decomposition to form any of the following impurities is less than 0.5%: a) bis(2-chloroethyl)amine hydrochloride; b) 3-(2-chloroethyl)-2-oxo-2-hydroxy-1,3,6,2-oxadiazaphosphonane; and c) 3-[2-(2-chloroethylamino)ethyl amino] propyl dihydrogen phosphate dihydrochloride. Essentially, the patent provides a composition with 70% or more of ethanol as the main solvent, and which requires a combination of polyethylene glycol and/or propylene glycol to provide a stable solution. The admitted scope of the patent is restricted to cyclophosphamide compositions wherein the carrier contains mainly ethanol, and where polyethylene glycol and propylene glycol are both present as cosolvents to provide a stable solution. Further, the patent specification does not provide stability data beyond 7 days, and so it is not clear if the composition would be stable over its shelf-life, and/or what the shelf-life would be.

U.S. Pat. No. 9,662,342 (Aurobindo) is directed to improved cyclophosphamide formulations and methods of making the same. It discloses a cyclophosphamide composition containing a substantially non-aqueous liquid carrier having extended stability, which carrier comprises an ethanolic solvent system consisting of ethanol, and an ethanol soluble acidifying agent wherein the cyclophosphamide and the ethanol soluble acidifying agent are solubilized in the ethanol with cyclophosphamide as the only pharmaceutically active ingredient. The specification does not teach nor support a composition that is stable and that does not use an ethanol soluble acidifying agent, i.e. citric acid. The working examples of the patent all require the presence of water as a carrier, or in the absence of water require a high volume of propylene glycol.

US20170143744 (DRL), published on May 25, 2017, claims a stable liquid pharmaceutical formulation of cyclophosphamide comprising cyclophosphamide and at least one pharmaceutically acceptable excipient, wherein moisture content of the liquid formulation is less than about 2.0% by weight, and the formulation is free of polyol. The specification states at para 0110—"Even in presence of non-aqueous solvents (which contribute to very less quantity of moisture or water content) also cyclophosphamide was not that stable. It was understood that probably the bound water of cyclophosphamide monohydrate (approximately 6.25%) may be responsible for hydrolytic degradation of cyclophosphamide in non-aqueous solvent such as anhydrous ethanol."

U.S. Ser. No. 10/849,916 (DRL), published on Dec. 1, 2020, relates to novel impurities of cyclophosphamide having structure V, VI or VII and a stabilized form of these novel impurities. The invention also encompasses a process of preparing a stabilized form of the impurities and isolating them. The invention is chiefly directed to cyclophosphamide formulations which include cyclophosphamide, at least one pharmaceutically acceptable excipient, and a defined level of these impurities having structure V, VI or VII. The exemplified liquid formulations of cyclophosphamide in the patent typically use an excipient selected from ethanol, Polysorbate 80, cyclodextrin, dimethyl acetamide, Cremophor and combinations thereof.

WO2020178725, published on Sep. 10, 2020, relates to a stable ready-to-use or a ready-to-dilute liquid composition comprising cyclophosphamide meant for parenteral administration, wherein the cyclophosphamide is dissolved in a solvent selected from dehydrated alcohol, dimethyl acetamide, polyethylene glycol, propylene glycol, water, glycerol and combinations thereof.

BRIEF SUMMARY OF THE INVENTION

In one embodiment, the present invention provides a stable ready-to-dilute composition of cyclophosphamide wherein the total impurities are not more than 4.0% over the shelf-life of the composition, when stored at 2-8 degrees Celsius.

In one embodiment, the present invention provides a ready-to-dilute composition of cyclophosphamide that is stable, and which is non-aqueous.

In one embodiment, the present invention provides a ready-to-dilute composition of cyclophosphamide that is stable, and which is free of propylene glycol.

DESCRIPTION

The present invention provides stable formulations of cyclophosphamide that are ready-to-dilute, and do not require reconstitution. Further, it saves significant time as the composition can be directly administered (bolus) or injected into a bag containing a large volume parenteral, and the time taken to prepare the dose is reduced. It must be noted that drugs like cyclophosphamide are administered to the patient in an out-patient chemotherapy setting, wherein the patient comes in and waits while the healthcare professional prepares the dose. Thus, if the waiting time is reduced through use of the ready-to-dilute composition of the present invention, the exposure of the patient to other patients, and to hospital-derived infections, is also reduced.

The present invention provides a ready-to-dilute composition of cyclophosphamide that is stable, and which provides the advantages of reduced dosing errors and ease of administration. The present invention provides a stable composition of cyclophosphamide comprising a therapeutically effective amount of cyclophosphamide, ethanol as solvent, polyethylene glycol as a solvent, and optionally, monothioglycerol as the anti-oxidant, wherein the composition is stable over its shelf-life.

The ready-to-dilute compositions of the present invention include cyclophosphamide in the form of its pharmaceutically acceptable salt or solvate. In preferred embodiments the cyclophosphamide is present in the form of cyclophosphamide monohydrate.

The compositions of the present inventions contain the cyclophosphamide or its pharmaceutically acceptable salt or solvate in an amount of about 100 mg to about 1000 mg by weight of anhydrous cyclophosphamide. In embodiments, the compositions comprise the cyclophosphamide or its pharmaceutically acceptable salt or solvate in an amount of about 200 mg to about 500 mg by weight of anhydrous cyclophosphamide. In embodiments, the compositions comprise the cyclophosphamide or its pharmaceutically acceptable salt or solvate in an amount of about 200 mg to about 400 mg by weight of anhydrous cyclophosphamide. In embodiments, the compositions comprise the cyclophosphamide or its pharmaceutically acceptable salt or solvate in an amount of about 200 mg to about 300 mg by weight of anhydrous cyclophosphamide. In embodiments, the compositions comprise the cyclophosphamide or its pharmaceutically acceptable salt or solvate in an amount of about 200 mg by weight of anhydrous cyclophosphamide.

The ready-to-dilute compositions of the present invention include a solvent that is critical to providing solubility and long term stability of the cyclophosphamide contained therein. The solvent used may be a single solvent or a mixture of one or more solvents. The pharmaceutically acceptable solvents that may be used in the ready-to-dilute compositions of the present invention may be selected from the group consisting of ethanol, polyethylene glycol or a mixture thereof. The solvents used in the compositions of the present invention do not include propylene glycol. Although the prior art, such as U.S. Pat. No. 9,662,342 (Aurobindo) and WO2020178725, taught use of propylene glycol as a solvent for cyclophosphamide, and although US20170143744 (DRL) taught polyol free compositions of cyclophosphamide, the inventors have found that stable ready-to-dilute compositions of cyclophosphamide can be obtained by (a) using polyethylene glycol (a glycol) and (b) by avoiding propylene glycol, and further wherein the amount of ethanol is kept below 60% of the total composition.

The ready-to-dilute compositions of the present invention use ethanol, preferably absolute ethanol, as a solvent for solubilizing cyclophosphamide or its pharmaceutically acceptable salt or solvate as the sole solvent, or it may use a combination of ethanol with polyethylene glycol. In preferred embodiments of the invention, the ready-to-dilute compositions of the present invention use ethanol and polyethylene glycol 400 as the solvent. The amount of ethanol that may be used ranges from about 40% to about 60% of the total compositions. The amount of polyethylene glycol 400 (PEG 400) that may be used is more than 30% of the total composition. Typically, the ratio of ethanol to PEG 400 ranges from 1:0.75 to 1:2.

The ready-to-dilute compositions of the present invention include monothioglycerol as an antioxidant. It may be present in an amount ranging from about 0.005% to about 0.05% of the total composition.

The term "shelf life" refers to the amount of time the pharmaceutical composition may be stored without loss of potency and/or performance profile. In some embodiments of the present invention, shelf life refers to the amount of time the pharmaceutical composition may be stored without loss of about 4%, about 3%, about 2% or about 1% of the potency and/or performance of the active, when stored at refrigerated conditions, i.e. about 2° C. to about 8° C. The stable compositions provided herein are designed to have shelf life of at least 24 months.

As discussed above, the cyclophosphamide ready-to-dilute composition of the present invention is stable over its shelf life. The specification for impurities in the ready-to-use composition, at shelf-life, when stored at about 2° C. to about 8° C., is as seen in Table 1 below

TABLE 1

Impurity specification at shelf-life for ready-to use compositions of the present invention

| Impurity | Specification |
| --- | --- |
| Related Compound B | Not more than 0.50% |
| Related Compound D | Not more than 0.50% |
| Related Compound E | Not more than 1.5% |
| Related Compound F | Not more than 1.5% |
| Any unspecified Impurity | Not more than 0.2% |
| Total Impurities | Not more than 4.0% |

The impurities are described in Table 2 below.

TABLE 2

| Name of Impurity | Chemical name of the impurity | Structure |
| --- | --- | --- |
| Related Compound B | 3-(2-Chloroethyl)-2-oxo-2-hydroxy-1,3,6,2-oxadiazaphosphonane | 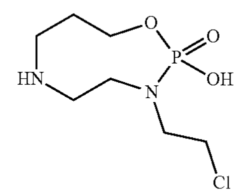 [SMILES: O=P1(O)OCCCNCCN1CCCl] |
| Related Compound D | 3-[2-(2-Chloroethyl-amino)ethylamino]propyl dihydrogen phosphate | 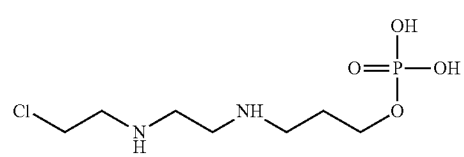 [SMILES: O=P(O)(O)OCCCNCCNCCCl] |
| Related Compound E | 2-((2-chloroethyl)(2-ethoxyethyl)amino)-1,3,2-oxazaphosphinane-2-oxide | 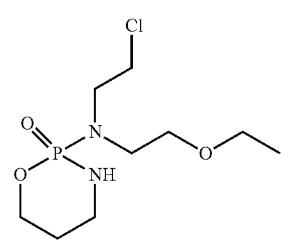 [SMILES: CCOCCN(CCCl)P1(=O)NCCCO1] |
| Related Compound F | 3-aminopropyl hydrogen (2-chloroethyl)(2-ethoxyethyl) phosphoramidate | 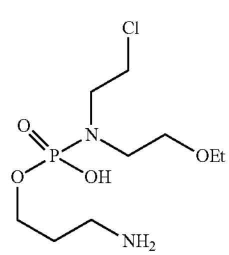 [SMILES: CCOCCN(CCCl)P(=O)(O)OCCCN] |

In preferred embodiments, the ready-to-dilute compositions of the present invention have no more than 4.0% of total impurities when stored at about 2 degrees Celsius to about 8 degrees Celsius.

In another embodiment, the ready-to-dilute composition of the present invention has no more than 0.50% of related compound B in the composition at the end of 24 months, when stored at about 2 degrees Celsius to about 8 degrees Celsius.

In yet another embodiment, the ready-to-dilute composition of the present invention has no more than 0.50% of related compound D in the composition at the end of 24 months, when stored at about 2 degrees Celsius to about 8 degrees Celsius.

In another embodiment, the ready-to-dilute composition of the present invention has no more than 1.5% of related compound E in the composition at the end of 24 months, when stored at about 2 degrees Celsius to about 8 degrees Celsius.

In one embodiment, the ready-to-dilute composition of the present invention has no more than 1.5% of related compound F in the composition at the end of 24 months, when stored at about 2 degrees Celsius to about 8 degrees Celsius.

In yet another embodiment, the ready-to-dilute composition of the present invention has no more than 0.2% of any unspecified impurity in the composition at the end of 24 months, when stored at about 2 degrees Celsius to about 8 degrees Celsius.

In one embodiment, the ready-to-dilute composition of the present invention has no more than 4.0% of total impurities and no more than 0.50% of related compound B in the composition at the end of 24 months, when stored at about 2 degrees Celsius to about 8 degrees Celsius.

In one embodiment, the ready-to-dilute composition of the present invention has no more than 4.0% of total impurities and no more than 0.50% of related compound D in the composition at the end of 24 months, when stored at about 2 degrees Celsius to about 8 degrees Celsius.

In one embodiment, the ready-to-dilute composition of the present invention has no more than 4.0% of total impurities and no more than 1.5% of related compound E in the composition at the end of 24 months, when stored at about 2 degrees Celsius to about 8 degrees Celsius.

In one embodiment, the ready-to-dilute composition of the present invention has no more than 4.0% of total impurities and no more than 1.5% of related compound F in the composition at the end of 24 months, when stored at about 2 degrees Celsius to about 8 degrees Celsius.

In one embodiment, the ready-to-dilute composition of the present invention has no more than 4.0% of total impurities and no more than 0.2% of any unspecified impurity in the composition at the end of 24 months, when stored at about 2 degrees Celsius to about 8 degrees Celsius.

In some embodiments, the ready-to-dilute compositions of the present invention have no more than 4.0% of total impurities, no more than 0.2% of any unspecified impurity and no more than 0.50% of related compound B in the composition at the end of 24 months, when stored at about 2 degrees Celsius to about 8 degrees Celsius.

In some embodiments, the ready-to-dilute compositions of the present invention have no more than 4.0% of total impurities, no more than 0.2% of any unspecified impurity and no more than 0.50% of related compound D in the composition at the end of 24 months, when stored at about 2 degrees Celsius to about 8 degrees Celsius.

In other embodiments, the ready-to-dilute compositions of the present invention have no more than 4.0% of total impurities, no more than 0.2% of any unspecified impurity and no more than 1.5% of related compound E in the composition at the end of 24 months, when stored at about 2 degrees Celsius to about 8 degrees Celsius.

In yet other embodiments, the ready-to-dilute compositions of the present invention have no more than 4.0% of total impurities, no more than 0.2% of any unspecified impurity and no more than 1.5% of related compound F in the composition at the end of 24 months, when stored at about 2 degrees Celsius to about 8 degrees Celsius.

In some embodiments, the ready-to-dilute compositions of the present invention have no more than 4.0% of total impurities, no more than 0.2% of any unspecified impurity, no more than 0.50% of related compound B and no more than 0.50% of related compound D in the composition at the end of 24 months, when stored at about 2 degrees Celsius to about 8 degrees Celsius.

In some embodiments, the ready-to-dilute compositions of the present invention have no more than 4.0% of total impurities, no more than 0.2% of any unspecified impurity, no more than 0.50% of related compound B, no more than 0.50% of related compound D and no more than 1.5% of related compound E in the composition at the end of 24 months, when stored at about 2 degrees Celsius to about 8 degrees Celsius.

In some embodiments, the ready-to-dilute compositions of the present invention have no more than 4.0% of total impurities, no more than 0.2% of any unspecified impurity, no more than 0.50% of related compound B, no more than 0.50% of related compound D and no more than 1.5% of related compound F in the composition at the end of 24 months, when stored at about 2 degrees Celsius to about 8 degrees Celsius.

In highly preferred embodiments, the ready-to-dilute compositions of the present invention have no more than 4.0% of total impurities, no more than 0.2% of any unspecified impurity, no more than 0.50% of related compound B, no more than 0.50% of related compound D, no more than 1.5% of related compound E and no more than 1.5% of related compound F in the composition at the end of 24 months, when stored at about 2 degrees Celsius to about 8 degrees Celsius.

The ready-to-dilute compositions of the present invention are prepared by aseptic process, wherein the dispensing and admixture of the excipients and cyclophosphamide is carried out under aseptic conditions under laminar flow conditions. Once the solution of the composition is obtained, it is sterilized by passing through 0.2µ polytetrafluoroethylene (PTFE) membrane filter and filled into vials. The vials used typically may be clear USP Type I glass vials that are pharmaceutically acceptable. The vials are stoppered with coated bromobutyl rubbers, followed by flip top aluminium seals.

The ready-to-dilute to compositions of the present invention are stored at about 2 degrees Celsius to about 8 degrees Celsius. When stored under these conditions, the compositions were found to remain stable, as defined herein, for at least 24 months.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

All publications, patent applications, patents, and other references mentioned are incorporated by reference herein in their entirety for all purposes.

As used herein, "a," "an," or "the" can mean one or more than one. For example, "a" solvent can mean a single solvent or a multiplicity of solvents.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound, related compound, impurity or agent of this invention, dose, time, temperature, and the like, is meant to encompass variations of ±10% of the specified amount.

The term "cyclophosphamide" may be used interchangeably with "cyclophosphamide and its pharmaceutically acceptable salt or solvate".

The present invention is further illustrated by reference to the following examples which are for illustrative purpose only and do not limit the scope of the invention in any manner.

EXAMPLES

Example 1

| Ingredients | Quantity/mL | % w/v |
|---|---|---|
| Cyclophosphamide | 200 mg | 20 |
| Monothioglycerol | 0.138 mg | 0.01 |
| Polyethylene glycol-400 | Qs to 1 mL | QS to 100 |

Example 2

| Ingredients | Quantity/mL | % w/v |
|---|---|---|
| Cyclophosphamide | 200 mg | 20 |
| Ethanol (99% USP) | 0.03-0.06 mL or 20 mg-50 mg | 2-5 |
| Monothioglycerol | 0.138 mg | 0.01 |
| Polyethylene glycol-400 | Qs to 1 mL | QS to 100 |

Example 3

| Ingredients | Quantity/mL | % w/v |
|---|---|---|
| Cyclophosphamide | 200 mg | 20 |
| Ethanol (99% USP) | 0.44-0.51 mL or 350-400 mg | 45-50 |
| Monothioglycerol | 0.138 mg | 0.01 |
| Polyethylene glycol 400 | Qs to 1 mL | QS to 100 |

For each of Examples 1, 2 and 3—All ingredients were dispensed as per the manufacturing formula and the required quantity of ethanol was transferred into a compounding vessel. The required quantity of Cyclophosphamide was added into the compounding vessel under stirring at about 400 to about 500 rpm to get a clear solution. Monothioglycerol was added into the above compounding vessel under stirring to get a clear solution. This was followed by addition of polyethylene glycol 400 and the volume was made up. The solution was stirred well to get a clear homogenous solution. The bulk solution was filtered through 0.2μ PTFE membrane filter and filled into vials (Fill vol: 2.5 mL and 5 mL), stoppered, and sealed.

The compositions of Examples 1, 2 and 3 were packaged in clear USP Type-1 glass vials, closed with coated bromobutyl rubber stoppers and flip top aluminium seals.

Example 4

The above exemplified formulations of cyclophosphamide were subjected to the stress stability test wherein the temperature was set at 40° C. for a time period of 5 days. The control used in the test is similar to the commercialized product of Ingenus Pharmaceuticals (disclosed and claimed in US 20180055861, and approved as NDA #212501 by the USFDA), which was prepared inhouse for the comparative testing. The Ingenus/control product includes 500 mg cyclophosphamide, 1.55 g Ethanol, 0.085 g Propylene Glycol, 0.085 g Polyethylene glycol 400 and 0.345 mg Monothioglycerol. The results of the stability testing are summarized in Table 3 below.

TABLE 3

Stress stability results of Cyclophosphamide injection (Stress at 40° C./5 days)

| Product | Ingenus product (control) | Example-1 | Example-2 | Example-3 |
|---|---|---|---|---|
| Total Impurities (% w/w) | 4.95 | 3.98 | 3.6 | 3.64 |

It was observed that the total impurity percentage was less than that for the control.

Example 5

The composition of Example 3 was charged for stability under two separate conditions of temperature and humidity and tested. The results are tabulated in Table 4 below.

TABLE 4

Stability Data of Cyclophosphamide Injection, 200 mg/mL

Fill volume: 2.5 mL

| Test | Initial | 2-8°C | | | | 25 ± 2° C./60 ± 5% RH | | | |
|---|---|---|---|---|---|---|---|---|---|
| | | 1M | 2M | 3M | 6M | 1M | 2M | 3M | 6M |
| Description | CCS | CCS | CCS | CCS | CCS | CCS | CCS | CCS | Pale yellow |
| pH | 3.98 | 3.91 | 4.45 | 4.25 | 4.45 | 4.44 | 4.44 | 4.15 | 3.70 |
| Assay (%) | 102.3 | 101.8 | 101.0 | 100.1 | 99.04 | 98.4 | 95.9 | 91.5 | 82.87 |
| Related Substances by HPLC (% w/w) | | | | | | | | | |
| Related compound-B | 0.05 | 0.09 | 0.09 | 0.11 | 0.12 | 0.22 | 0.28 | 0.21 | 0.15 |
| Related compound-D | 0.01 | 0.05 | 0.04 | 0.03 | ND | 0.12 | 0.14 | 0.12 | 0.12 |
| Related Compound-E | ND | 0.11 | 0.16 | 0.20 | 0.26 | 0.56 | 1.10 | 1.52 | 2.51 |
| Related Compound-F | 0.02 | 0.30 | 0.32 | 0.37 | 0.6 | 1.36 | 2.75 | 3.00 | 6.67 |
| Any unspecified impurity | 0.01 | 0.04 | 0.02 | 0.04 | 0.07 | 0.08 | 0.26 | 0.30 | 0.87 |
| Total Impurities | 0.46 | 0.71 | 0.67 | 0.80 | 1.14 | 2.67 | 5.29 | 6.41 | 14.11 |

ND: Not Detected; CCS: Clear colorless solution

The invention claimed is:

1. A stable ready-to-dilute composition comprising (i) cyclophosphamide or its pharmaceutically acceptable salt or solvate in an amount ranging from about 100 mg to about 1000 mg, (ii) about 40% to about 60% (w/v) of ethanol, (iii) about 0.005% to about 0.05% (w/v) of monothioglycerol as an antioxidant and (iv) more than 30% (w/v) of polyethylene glycol 400; wherein the ratio of ethanol to polyethylene glycol 400 is from 1:0.75 to 1:2, wherein the composition has no more than 4.0% of total impurities, no more than 0.2% of any unspecified impurity, no more than 0.50% of 3-(2-Chloroethyl)-2-oxo-2-hydroxy-1, 3, 6, 2-oxadiazaphosphonane (related compound B), no more than 0.50% of 3-[2-(2-Chloroethylamino) ethylamino] propyl dihydrogen phosphate (related compound D), no more than 1.5% of 2-((2-chloroethyl) (2-ethoxyethyl) amino)-1,3,2-oxazaphosphinane-2-oxide (related compound E) and no more than 1.5% of 3-aminopropyl hydrogen (2-chloroethyl)(2-ethoxyethyl) phosphoramidate (related compound F) when stored in a vial at about 2 degrees Celsius to about 8 degrees Celsius for at least 3 months.

2. The stable ready-to-dilute composition of claim 1, wherein the composition has a volume of 1 mL.

3. A stable ready-to-dilute composition consisting of (i) cyclophosphamide or its pharmaceutically acceptable salt or solvate in an amount ranging from about 100 mg to about 1000 mg, (ii) about 40% to about 60% (w/v) of ethanol, (iii) about 0.005% to about 0.05% (w/v) of monothioglycerol as an antioxidant and (iv) polyethylene glycol 400 qs to 100% volume, wherein the composition has no more than 4.0% of total impurities, no more than 0.2% of any unspecified impurity, no more than 0.50% of 3-(2-Chloroethyl)-2-oxo-2-hydroxy-1, 3, 6, 2-oxadiazaphosphonane (related compound B), no more than 0.50% of 3-[2-(2-Chloroethylamino) ethylamino] propyl dihydrogen phosphate (related compound D), no more than 1.5% of 2-((2-chloroethyl) (2-ethoxyethyl) amino)-1,3,2-oxazaphosphinane-2-oxide (related compound E) and no more than 1.5% of 3-aminopropyl hydrogen (2-chloroethyl)(2-ethoxyethyl) phosphoramidate (related compound F) when stored for 3 months in a vial at about 2 degrees Celsius to about 8 degrees Celsius.

4. The stable ready-to-dilute composition of claim 1, wherein the composition comprises cyclophosphamide or its pharmaceutically acceptable salt or solvate in an amount ranging from about 100 mg to about 500 mg.

5. The stable ready-to-dilute composition of claim 1, wherein the composition comprises cyclophosphamide or its pharmaceutically acceptable salt or solvate in an amount ranging from about 200 mg to about 400 mg.

6. The stable ready-to-dilute composition of claim 3, wherein the composition consists of cyclophosphamide or its pharmaceutically acceptable salt or solvate in an amount ranging from about 100 mg to about 500 mg.

7. The stable ready-to-dilute composition of claim 3, wherein the composition consists of cyclophosphamide or its pharmaceutically acceptable salt or solvate in an amount ranging from about 200 mg to about 400 mg.

8. The stable ready-to-dilute composition of claim 3, wherein the composition has a volume of 1 mL.

9. The stable ready-to-dilute composition of claim 1, wherein the composition is free of propylene glycol.

10. The stable ready-to-dilute composition of claim 3, wherein the composition is free of propylene glycol.

* * * * *